(12) United States Patent
Luce

(10) Patent No.: US 8,613,704 B2
(45) Date of Patent: Dec. 24, 2013

(54) SUBSYSTEMS AND METHODS FOR NON-CONTACT CORNEAL DEFORMATION

(75) Inventor: David A. Luce, Clarence Center, NY (US)

(73) Assignee: Reichert, Inc., Depew, NY (US)

( * ) Notice: Subject to any disclaimer, the term of this patent is extended or adjusted under 35 U.S.C. 154(b) by 249 days.

(21) Appl. No.: 13/013,102

(22) Filed: Jan. 25, 2011

(65) Prior Publication Data

US 2012/0190961 A1 Jul. 26, 2012

(51) Int. Cl.
*A61B 3/16* (2006.01)

(52) U.S. Cl.
CPC ........................................ *A61B 3/165* (2013.01)
USPC ......................................................... 600/401

(58) Field of Classification Search
USPC ........................................................... 600/401
See application file for complete search history.

(56) References Cited

U.S. PATENT DOCUMENTS

| | | | | |
|---|---|---|---|---|
| 3,181,351 | A * | 5/1965 | Stauffer | 600/401 |
| 3,232,099 | A * | 2/1966 | Motchenbacher | 600/401 |
| 3,585,849 | A * | 6/1971 | Grolman | 600/401 |
| 4,386,611 | A * | 6/1983 | Kantorski et al. | 600/401 |
| 5,779,633 | A | 7/1998 | Luce | |
| 5,989,195 | A * | 11/1999 | Iijima et al. | 600/561 |
| 6,361,495 | B1 * | 3/2002 | Grolman | 600/401 |
| 6,616,609 | B2 | 9/2003 | Siskowski et al. | |
| 6,726,625 | B2 * | 4/2004 | Luce | 600/401 |
| 7,771,353 | B2 * | 8/2010 | Luce | 600/398 |
| 7,798,962 | B2 * | 9/2010 | Luce | 600/405 |
| 7,909,765 | B2 * | 3/2011 | Luce | 600/405 |
| 8,216,140 | B2 * | 7/2012 | Gur et al. | 600/401 |
| 2001/0051770 | A1 * | 12/2001 | Falck et al. | 600/398 |
| 2003/0086058 | A1 * | 5/2003 | Percival et al. | 351/208 |
| 2003/0088169 | A1 | 5/2003 | Percival et al. | |
| 2003/0088170 | A1 * | 5/2003 | Siskowski et al. | 600/399 |
| 2003/0088171 | A1 * | 5/2003 | Siskowski et al. | 600/401 |
| 2003/0097053 | A1 * | 5/2003 | Itoh | 600/401 |
| 2003/0191382 | A1 * | 10/2003 | Luce et al. | 600/401 |
| 2006/0217611 | A1 * | 9/2006 | Falck et al. | 600/406 |
| 2007/0055121 | A1 * | 3/2007 | Luce | 600/405 |
| 2007/0211212 | A1 * | 9/2007 | Bennwik | 351/221 |
| 2008/0077000 | A1 * | 3/2008 | Falck et al. | 600/406 |
| 2008/0165321 | A1 * | 7/2008 | Mimura et al. | 351/208 |
| 2010/0145180 | A1 * | 6/2010 | Abreu | 600/399 |

OTHER PUBLICATIONS

WIPO, Written Opinion of the International Searching Authority in International Application No. PCT/US2012/021166, mailed May 16, 2012.

* cited by examiner

*Primary Examiner* — Sean Dougherty
*Assistant Examiner* — Michael C Stout
(74) *Attorney, Agent, or Firm* — Hodgson Russ LLP

(57) ABSTRACT

An ophthalmic instrument that discharges a fluid pulse to deform the cornea of a test subject is improved by reducing the working distance between a nosepiece or a discharge tube from which the fluid pulse is discharged and the eye of the test subject. The invention improves measurement repeatability and patient comfort.

3 Claims, 6 Drawing Sheets

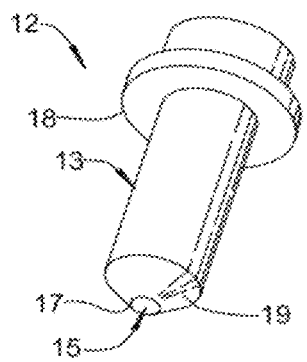
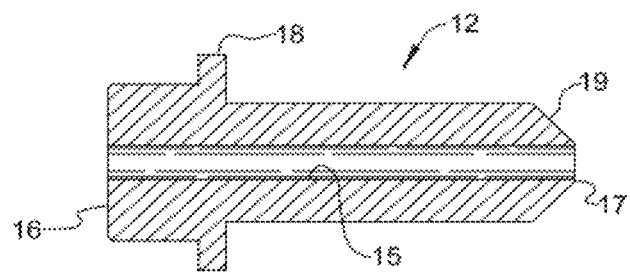
Fig. 4     Fig. 5
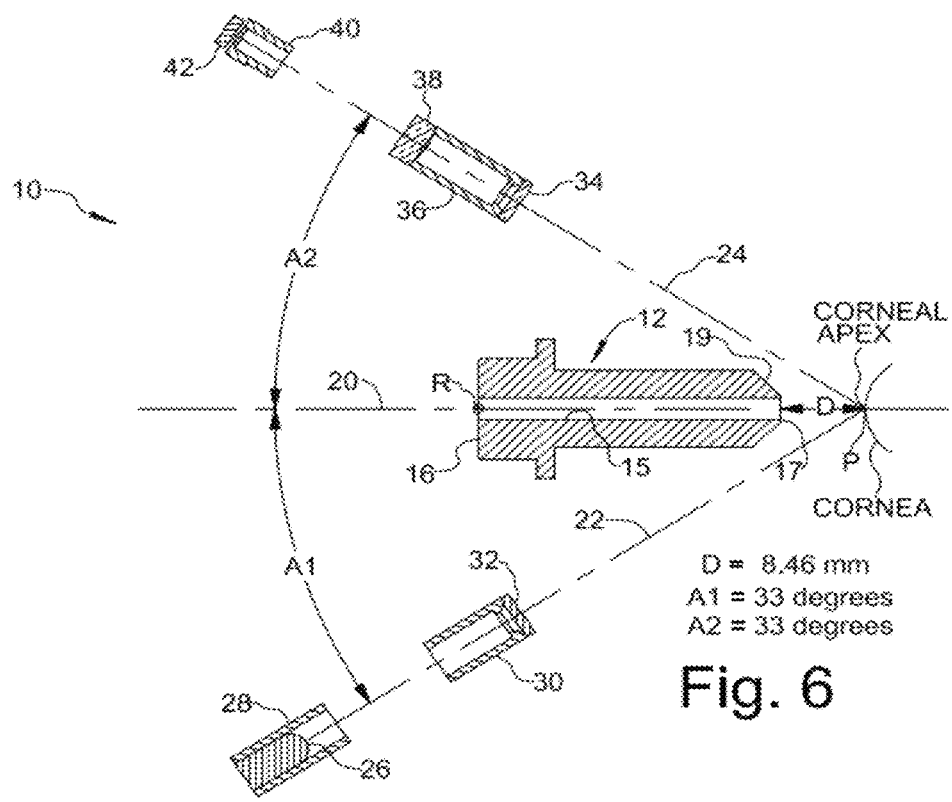
Fig. 6

SUBSYSTEMS AND METHODS FOR NON-CONTACT CORNEAL DEFORMATION

FIELD OF THE INVENTION

The present invention relates generally to ophthalmic instruments that deform the cornea using a fluid pulse, typically an air jet, directed at the eye. These instruments include non-contact tonometers ("NCTs") for measuring intraocular pressure ("IOP"), instruments for measuring the biomechanical properties of the cornea, and instruments capable of making both types of measurements.

BACKGROUND OF THE INVENTION

Traditional air jet NCTs, first developed in the 1960s, have used a single indentation eye-flattening event ("applanation") to measure IOP. During an NCT measurement, an air jet generated by a pump mechanism is discharged through a passage in a nosepiece of the NCT at the eye. The air jet creates an increasing pressure on the eye to a level that is adequate to deform the cornea through a first applanated state to a slightly concave state. Subsequently, as the air jet becomes disorganized, the pressure applied to the eye decreases to zero, and the cornea returns through a second applanated state to its original convex shape. IOP is calculated using an internal plenum pressure in the air jet pump mechanism that has a known (predetermined) correlation with the actual pressure exerted on the eye at the moment of inward applanation.

FIGS. 1-3 illustrate a nosepiece 2 and measurement subsystem 1 of a prior art NCT. Nosepiece 2 includes a nosepiece body 3 and a fluid discharge tube 4 held within nosepiece body 3. Fluid discharge tube 4 defines a fluid discharge passage 5 extending from an entry end 6 to an exit end 7 of the nosepiece. Nosepiece 2 is mounted in a measurement head of the NCT at a reference point R. A flange 8 may be provided on nosepiece 2 to facilitate secure mounting. Discharge passage 5 is in flow communication with a fluid pump mechanism of the NCT (not shown).

In preparation for an NCT measurement, the nosepiece 2 of the NCT is aligned with the eye in three dimensions. The fluid pulse discharge passage 5 through the nosepiece defines a fluid pulse axis 20 along which the fluid pulse is directed when it is discharged. The nosepiece 2 is aligned in X (up and down in FIG. 3) and Y (normal to the drawing sheet plane in FIG. 3) directions such that the fluid pulse axis 20 is normal to an apex of the cornea. Additionally, the nosepiece is aligned in a Z direction (left and right in FIG. 3) at a predetermined "working distance" D from the corneal apex defined as the distance along the fluid pulse axis 20 from a fluid exit end of discharge tube 4 (the end arranged flush with the exit end 7 of the nosepiece) to the corneal apex.

In addition to nosepiece 2, subsystem 1 comprises an optical applanation detection apparatus. The applanation detection apparatus includes an emitter 26 arranged and configured to provide a collimated beam along an illumination axis 22 converging with fluid pulse axis 20 at a target point P located a predetermined distance beyond the exit end 7 of nosepiece 2 along the fluid pulse axis. In the arrangement shown in FIG. 3, emitter 26 is an LED surrounded by a sleeve 28 and positioned upstream from an aperture stop tube 30 carrying a window 32. Subsystem 1 further comprises a light-sensitive detector 42 arranged on a detection axis 24 converging with illumination axis 22 and fluid pulse axis 20 at target point P. In the arrangement of FIG. 3, detector 42 is located behind an aperture tube 40, focusing lens 38, aperture stop tube 36, and window 34 all aligned on detection axis 24. The collimated illumination beam obliquely incident to the cornea along illumination axis 22 will be reflected by the corneal surface. When the corneal surface is curved, the collimated illumination beam will be fanned out upon reflection from the curved surface such that only a small portion of the illumination light reaches detector 42. However, when the cornea is applanated to provide a flat reflection surface, the illumination beam will remain collimated and will be reflected along detection axis 24 to reach detector 42 with minimal loss, and the detector 42 will register a sharp peak in intensity corresponding to the applanation event. The applanation detection apparatus described above will be familiar to those skilled in the NCT art. When the NCT is properly aligned for measurement, target point P (intersection of illumination, detection, and fluid pulse axes) coincides with the corneal apex such that the working distance D and the predetermined distance from exit end 8 of nosepiece 2 to target point P are the same distance.

Heretofore, conventional NCTs known to applicant have used a working distance D slightly greater than 11 mm. With proper instrument design, the conventional working distance provides a relative low value of high frequency noise with respect to the increasing pressure applied to the cornea by the fluid pulse. However, it has been discovered that at the conventional working distance of 11 mm, the applied external pressure function becomes quite "noisy" relative to the internal plenum pressure of the pump mechanism as the external pressure applied to the cornea by the fluid pulse decreases. Consequently, accurate correlation between the internal and external pressures is compromised. This has not been a problem for conventional NCTs, which use the initial inward applanation event associated with increasing pulse pressure as the sole basis for determining IOP, and disregard the subsequent outward applanation event associated with decreasing pulse pressure.

However, the problem was recently discovered in connection with a new generation of NCTs that use both the inward applanation event and a subsequent outward applanation event associated with decreasing pulse pressure in determining IOP. These "bi-directional" NCTs were developed by Reichert, Inc., assignee of the present invention, and have been described in U.S. Pat. Nos. 7,481,767; 6,817,981; and 6,419,631. High-frequency noise in the decreasing pressure function is a serious problem for bi-directional NCTs because the corneal-compensated IOP (so-called "IOPcc") is 2.5 times more sensitive to fluctuations in the second applanation signal than conventional IOP measurements are to fluctuations in the first applanation signal. The second applanation event occurs during the decreasing pressure period.

In principle, this problem could be resolved by simply increasing the conventional air tube diameter (about 2.4 mm) significantly. However, this potential solution creates other problems. These include the need for additional power to drive the pump system, increased vibration and noise due to larger forces generated in the pump, added costs and, most seriously, a significantly increased total force exerted on the eye since the area of application of the pulse pressure would increase. Historically, the major objection to the use of NCTs to measure IOP has been the test subject's neural response to the force of the air jet on the eye during a measurement. The most sensitive nerves responsive to an applied force in the human body are on the surface of the cornea. Therefore, for sake of patient comfort, it is important to avoid an increase in force (pressure times area) on the eye during a measurement as would occur with a larger diameter air tube.

The reason for the "noise" in the decreasing pressure time period is that the fluid pulse is losing collimation and beginning to dissipate where the fluid flow becomes chaotic and unstable. It should be noted that the breakup (noise) of the air jet can be measured with Reichert, Inc.'s tonometer calibration tool described in U.S. Pat. No. 6,679,842. The tonometer calibration tool provides a measurement of the force exerted on a surface located at the working distance of the NCT.

SUMMARY OF THE INVENTION

The invention is embodied in measurement subsystems for an ophthalmic instrument, methods of causing corneal applanation, and a method of improving an ophthalmic instrument through retrofit. The invention reduces a working distance between a fluid discharging nosepiece or discharge tube of the instrument and the cornea.

A subsystem of the invention generally comprises a nosepiece, and emitter, and a detector. The nosepiece includes an exit end and a fluid discharge passage configured to discharge a fluid pulse from the exit end of the nosepiece along a fluid pulse axis. The emitter is arranged and configured to provide a collimated beam along an illumination axis converging with the fluid pulse axis at a target point located at a predetermined distance beyond the exit end of the nosepiece along the fluid pulse axis. The detector is arranged on a detection axis converging with the illumination axis and the fluid pulse axis at the target point. The emitter and detector are used to optically detect corneal applanation in a known manner. The subsystem is characterized by the fact that the predetermined distance of the target point from the exit end of the nosepiece is less than 11 mm, and is preferably in a range from 8 mm through 9 mm.

An inventive method of causing corneal applanation using the subsystem summarized above comprises the steps of providing a nosepiece including an exit end and a fluid discharge passage configured to discharge a fluid pulse from the exit end of the nosepiece along a fluid pulse axis, aligning the nosepiece relative to the cornea such that the fluid pulse axis is normal to an apex of the cornea and the exit end of the nosepiece is less than 11 mm from the apex of the cornea as measured along the fluid pulse axis, and discharging a fluid pulse from the exit end of the nosepiece along the fluid pulse axis, wherein the fluid pulse causes applanation of the cornea.

In another subsystem of the invention, the nosepiece includes a discharge tube axially displaceable along the fluid pulse axis relative to a fixed nosepiece body, wherein the discharge tube is temporarily moved such that the tube extends beyond an exit end of the nosepiece body for discharging a fluid pulse. The discharge tube may be moved by force from fluid flow directed into the tube to generate the fluid pulse, or by a motor drive such as a solenoid.

A method of causing applanation of a cornea using the subsystem summarized in the immediately preceding paragraph comprises the steps of providing a nosepiece including a nosepiece body and fluid discharge tube axially movable relative to the nosepiece body, having an exit end and a guide passage, the nosepiece further including a fluid discharge tube having a fluid discharge passage configured to discharge a fluid pulse along a fluid pulse axis and a fluid exit end from which the fluid pulse is discharged, wherein the fluid discharge tube is movable along the fluid pulse axis relative to the nosepiece body; aligning the nosepiece relative to the cornea such that the fluid pulse axis defined by the discharge tube is normal to an apex of the cornea and an exit end of the nosepiece body is not less than 11 mm from the apex of the cornea as measured along the fluid pulse axis, causing the fluid discharge tube to move along the fluid pulse axis relative to the nosepiece body such that a fluid exit end of the discharge tube is less than 11 mm from the apex of the cornea, and discharging a fluid pulse from the fluid exit end of the fluid discharge tube, wherein the fluid pulse causes applanation of the cornea.

The method of improving an ophthalmic instrument through retrofit is accomplished by replacing a prior nosepiece with a new longer nosepiece mounted at the same location as the prior nosepiece.

The present invention improves measurement repeatability because the behavior of the fluid pulse in applying pressure on the cornea as a function of time is more uniform, particularly as the applied pressure decreases. An unanticipated advantage of the invention is that the force of the fluid pulse on the eye is actually reduced even though the working distance at which the pulse is discharged is closer to the eye.

BRIEF DESCRIPTION OF THE DRAWINGS

The nature and mode of operation of the present invention will now be more fully described in the following detailed description of the invention taken with the accompanying drawing figures, in which:

FIG. 4 is a perspective view of an ophthalmic non-contact applanation nosepiece formed in accordance with an embodiment of the present invention;

FIG. 5 is a cross-sectional view of the nosepiece shown in FIG. 4;

FIG. 6 is a schematic view of an ophthalmic non-contact applanation measurement subsystem using the nosepiece shown in FIGS. 4 and 5;

DETAILED DESCRIPTION OF THE INVENTION

Figure 1:
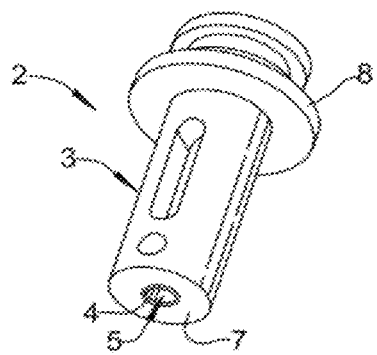
FIG. 1 is a perspective view of an NCT nosepiece formed in accordance with prior art.
Figure 2:
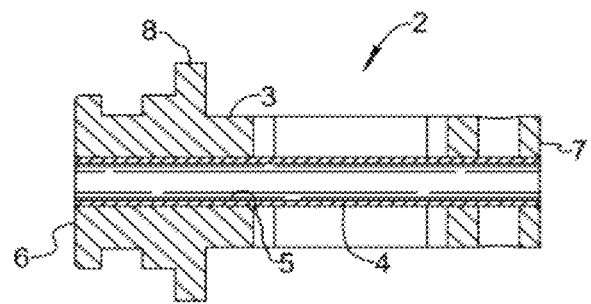
FIG. 2 is a cross-sectional view of the prior art nosepiece shown in FIG. 1.

FIGS. 4 and 5 show a nosepiece 12 formed in accordance with an embodiment of the present invention, and FIG. 6 illustrates a tonometer measurement subsystem 10 of the present invention that comprises nosepiece 12.

Nosepiece 12 includes an entrance end 16, an exit end 17, and a fluid discharge passage 15 extending through nosepiece 12 from entrance end 16 to exit end 17. Fluid discharge passage 15 is configured to discharge a fluid pulse from exit end 17 along a fluid pulse axis 20 to cause applanation of a cornea of a test subject. Nosepiece 12 may include a flange 18 useful for securely mounting the nosepiece in a measurement head of a non-contact tonometer or other ophthalmic instrument (not shown). Nosepiece may also have a tapered region 19 adjacent and converging toward exit end 17. The purpose of tapered region 19 will become apparent from the description of tonometer measurement subsystem 10 given below. As will be understood by those skilled in the art of non-contact tonometers, fluid discharge passage 15 is arranged in communication with a pump mechanism (not shown) operable to generate a fluid pulse which is conveyed through passage 15 until it is discharged along fluid pulse axis 20 at the cornea.

Subsystem 10, shown in FIG. 6, is the same as subsystem 1 of the prior art (FIG. 3) except that nosepiece 2 of the prior art is replaced by nosepiece 12 of the present invention. In the embodiment shown, entrance end 16 of nosepiece 12 is located at reference point R and flange 18 is seated at the same location as flange 8 of prior art nosepiece 2. In this way, the present invention may be practiced simply by retrofitting an existing tonometer or ophthalmic instrument with a new nosepiece 12.

New nosepiece 12 is longer from entrance end to its exit end than old nosepiece 2. As mentioned above in connection with FIG. 3, illumination axis 22 and detection axis 24 intersect at a common target point P on fluid pulse axis 20. Target point P is located a predetermined distance beyond the exit end of the nosepiece along fluid pulse axis 20. Consequently, the working distance D of measurement subsystem 10 is shorter than that of measurement subsystem 1 of the prior art. In a tested embodiment of the invention, new nosepiece 12 was made 3 mm longer than old nosepiece 2, thereby reducing the working distance D from 11.46 mm to 8.46 mm. When tonometer subsystem 12 is properly aligned with the cornea just before measurement, target point P coincides with an apex of the cornea as shown in FIG. 6 and the predetermined distance becomes the working distance D.

Nosepiece 12 and the other components of subsystem 10 may be aligned with the cornea of a test subject using an opto-electronic alignment system formed in accordance with one of the following commonly-owned U.S. patents, the entire disclosures of which are hereby incorporated by reference into the present specification for their teachings of various alignment systems and fluid pulse firing (discharge) systems: U.S. Pat. No. 4,881,807 entitled "Optical Alignment System"; U.S. Pat. No. 6,361,495 entitled "Hand-Held Non-Contact Tonometer"; U.S. Pat. No. 6,623,429 entitled "Hand-Held Non-Contact Tonometer"; U.S. Pat. No. 6,669,340 entitled "Alignment System for an Ophthalmic Instrument"; U.S. Pat. No. 6,749,302 entitled "Afocal Position Detection System and Ophthalmic Instrument Employing said System." Alignment is achieved when fluid pulse axis 20 intersects the corneal apex normal to the corneal surface, and the exit end 17 of nosepiece 12 is at the proper working distance from the cornea such that target point P coincides with the corneal apex. The alignment systems referenced above communicate with an automatic discharge mechanism for firing the fluid pulse as soon as alignment is achieved.

While the embodiment shown in FIG. 6 provides a working distance of 8.46 mm, other embodiments are possible wherein a different working distance is used and the position of target point P relative to exit end 17 is adjusted to equal the intended working distance. In accordance with the present invention, a working distance D less than 11 mm will improve uniformity of the pressure-versus-time function. Further improvement is realized at a working distance not greater than 10 mm. A currently preferred working distance between 8 mm and 9 mm provides substantial improvement in the pressure-versus-time function. It has been found that the benefits of further decreasing the working distance to less than 8 mm are outweighed by interference of the nosepiece with the patient's eyelash and the blink reflex that ensues.

Another factor that limits proximity of the nosepiece to the eye is the applanation detection apparatus, which requires space for the illumination beam incident along illumination axis 22 and the corneally reflected beam traveling along detection axis 24. In the embodiment shown, nosepiece 12 is provided with tapered region 19 adjacent and converging toward exit end 17 to accommodate the beam paths of the applanation detection apparatus.

The present invention is also embodied by a simple method of improving an ophthalmic instrument. In accordance with the method, a prior nosepiece is removed from the ophthalmic instrument, wherein the prior nosepiece includes an entry end located at a mounting location on the ophthalmic instrument, and a new longer nosepiece is installed with its entry end located at the same mounting location on the ophthalmic instrument. Following the nosepiece replacement, the ophthalmic instrument must be recalibrated in a known manner, for example by using the tonometer calibration tool referenced above.

Figure 7:
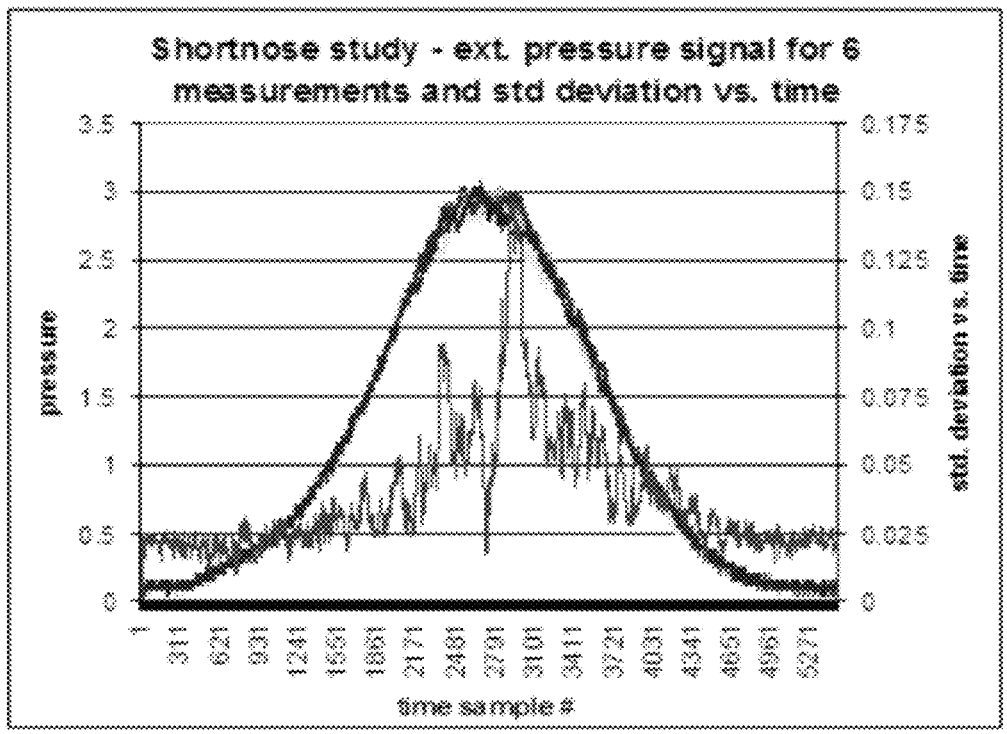
FIG. 7 is a plot of fluid pulse pressure versus time for six different fluid pulses discharged from an NCT of the prior art, with a superimposed plot of the standard deviation of the six pressure signals.
Figure 8:
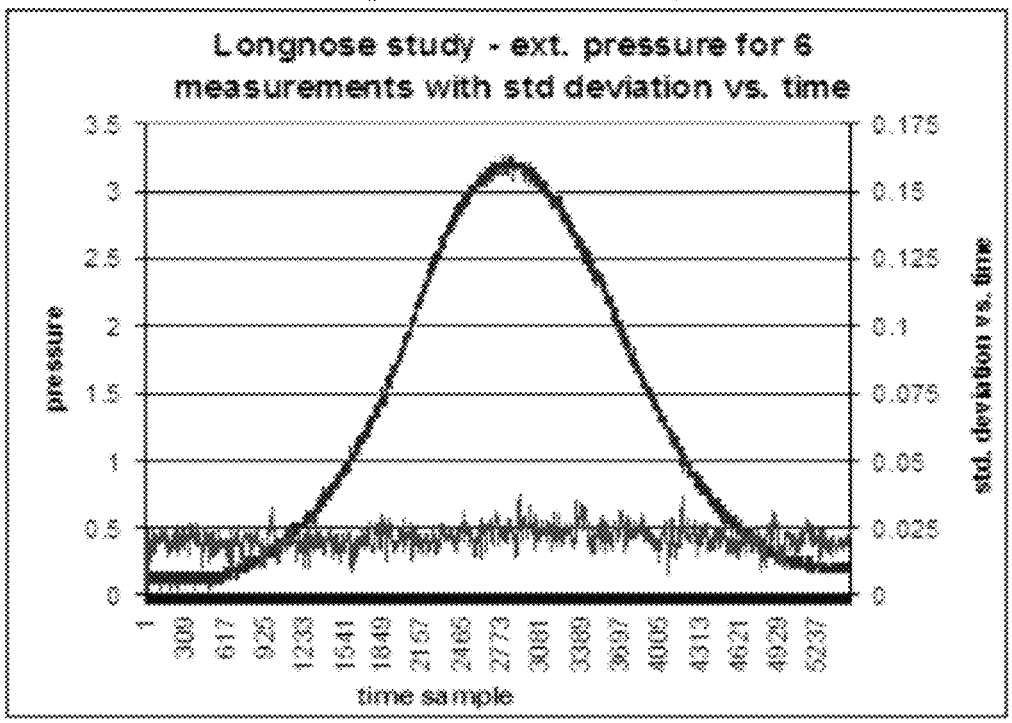
FIG. 8 is a plot similar to that of FIG. 7, wherein the fluid pulses were discharged from an NCT modified in accordance with the present invention.

Reference is now made to FIGS. 7 and 8 to explain how the present invention solves the recently discovered problem involving poor measurement repeatability. FIG. 7 is a plot of six air jets sequentially discharged from a Reichert 7CR tonometer manufactured by Reichert, Inc. of Depew, N.Y. using a short nosepiece of the prior art. The air jets were measured using a tonometer calibration tool (mentioned above) clipped on to the instrument. Six generally bell-shaped curves representing pressure applied by the air jet versus time for each respective air jet are plotted in FIG. 7. In addition, the standard deviation of the six pressure measurements is superimposed to in the plot to illustrate the tendency for increased variation among the air jets during the decreasing pressure time frame after the pressure curve has peaked. FIG. 8 is a the same type of plot as FIG. 7, wherein a longer nosepiece of the present invention was installed on the same Reichert 7CR instrument used in FIG. 7, and the same tonometer calibration tool was mounted thereon. The six air jets in FIG. 8 were measured within an hour of measuring the air jets in FIG. 7. As may be seen, the shorter working distance realized using the longer nosepiece greatly reduces variation among the applied pressure curves as reflected by the relatively flat and lower amplitude standard deviation plot. As may be understood, lower variation in the discharged air jets improves measurement repeatability.

Figure 9:
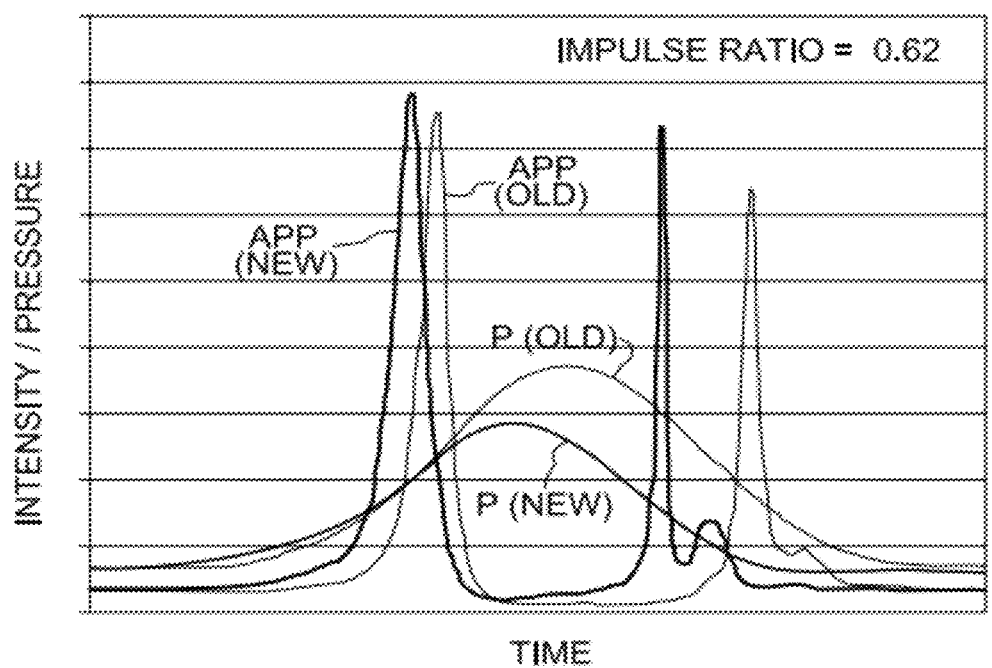
FIG. 9 is a plot showing superimposed pressure and applanation signals for an NCT measurement according to the prior art and an NCT measurement according to the present invention.

FIG. 9 illustrates how the present invention helps solve the recognized problem of patient discomfort. Curves APP (OLD) and APP (NEW) are applanation signals derived from detector 42 for prior art and inventive systems. Curves P (OLD) and P (NEW) are corresponding plenum pressure measurements from the instrument's pump mechanism. As will be seen, the closer working distance of the present invention achieves applanation at a lower pump plenum pressure than the working distance of the prior art. The total impulse delivered to the eye (the product of force times pulse duration), represented by the area under each bell-shaped plenum pressure curve P (OLD) and P (NEW), is significantly reduced. In FIG. 9, the impulse delivered by an instrument embodying the present invention is only 62% of the impulse delivered by a comparable prior art instrument. Thus, moving the exit end of the nosepiece closer to the patient does not add to patient discomfort, it actually reduces patient discomfort and is related to the earlier shutdown of the pump triggered by the occurrence of the earlier first applanation event.

Figure 3:
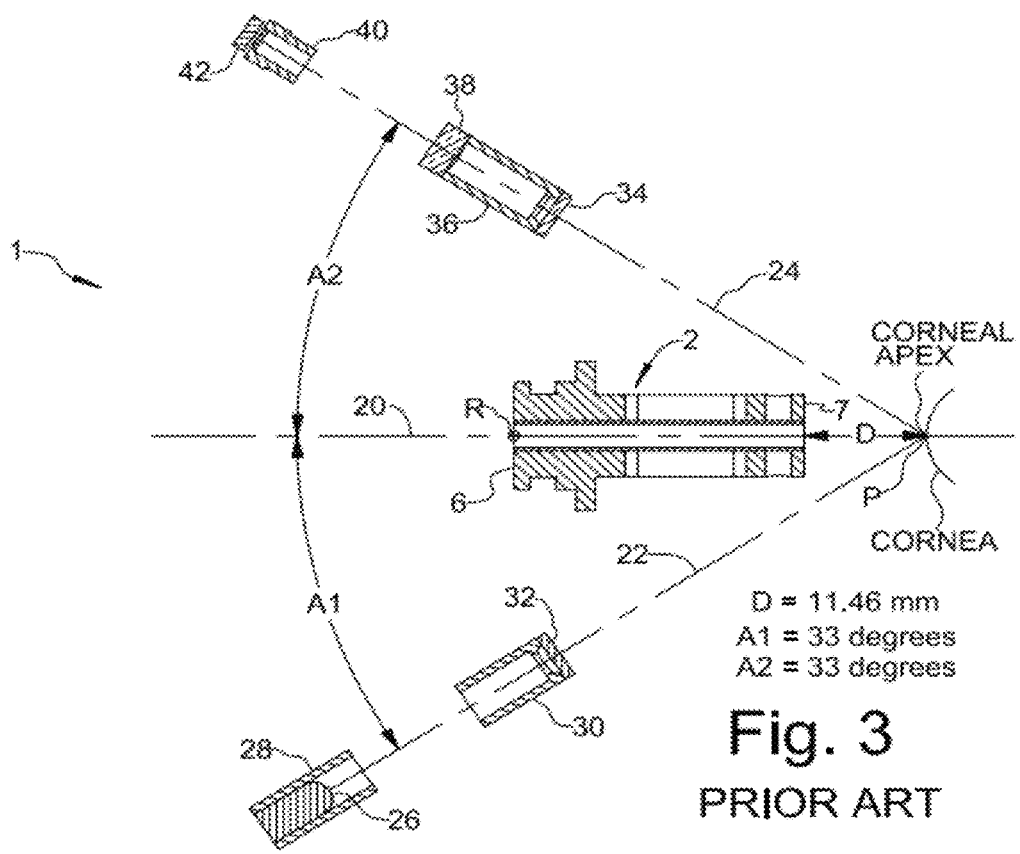
FIG. 3 is a schematic view of an NCT measurement subsystem of the prior art using the nosepiece shown in FIGS. 1 and 2.
Figure 10:
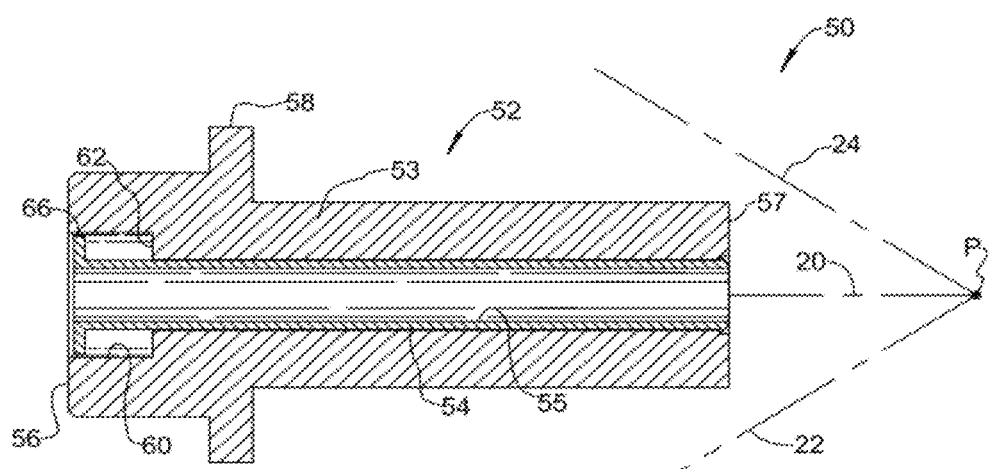
FIG. 10 is an enlarged view of an ophthalmic non-contact applanation measurement subsystem in accordance with another embodiment of the present invention, wherein a nosepiece of the subsystem is shown in an alignment configuration prior to fluid pulse discharge.
Figure 11:
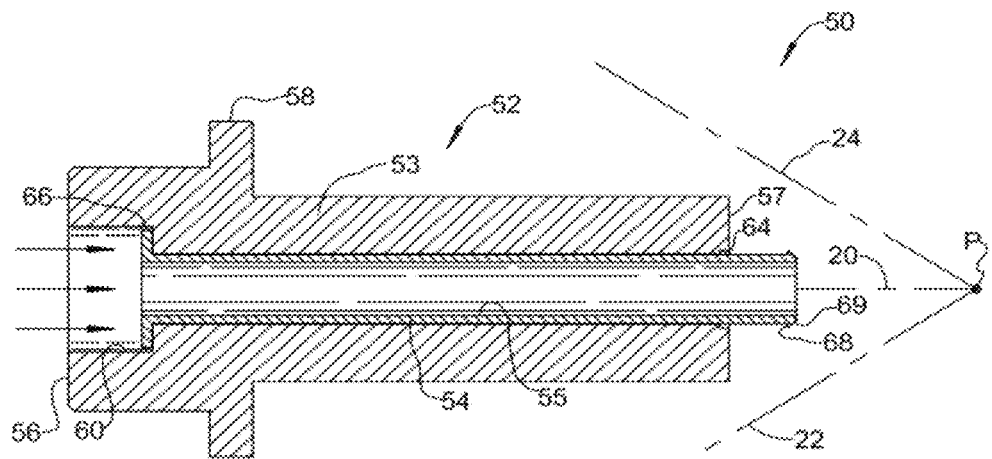
FIG. 11 is a view similar to that of FIG. 10, wherein the nosepiece is shown in a fluid pulse discharge configuration.
Figure 12:
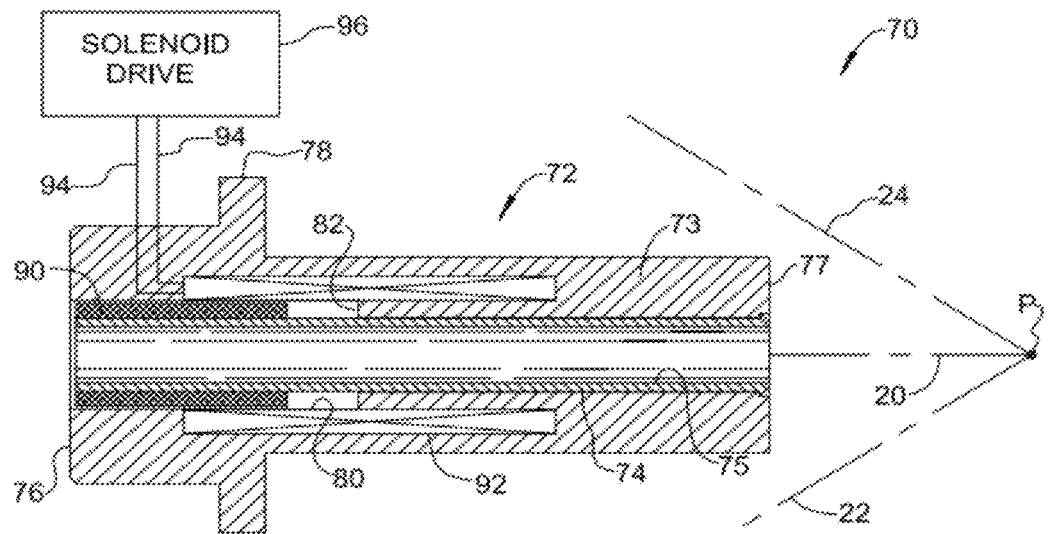
FIG. 12 is an enlarged view of an ophthalmic non-contact applanation measurement subsystem in accordance with a further embodiment of the present invention, wherein a nosepiece of the subsystem is shown in an alignment configuration prior to fluid pulse discharge.
Figure 13:
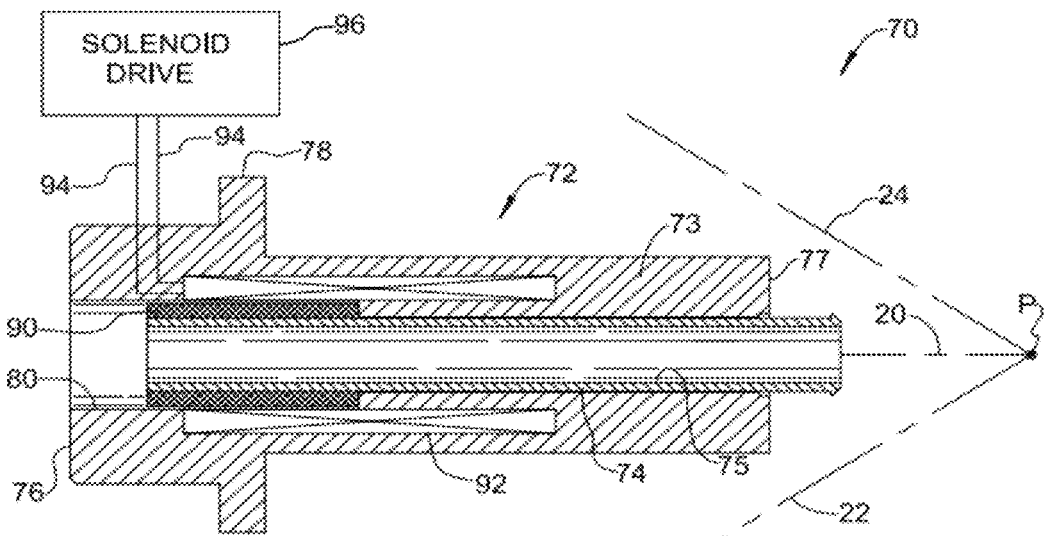
FIG. 13 is a view similar to that of FIG. 12, wherein the nosepiece is shown in a fluid pulse discharge configuration.

FIGS. 10-13 illustrate other embodiments wherein the working distance is reduced by temporarily extending a movable fluid discharge tube from a fixed body of the nosepiece. Subsystem 50 shown in FIGS. 10-11 and subsystem 70 shown in FIGS. 12-13 are similar to one another, but use different means for moving the fluid discharge tube relative to the fixed nosepiece body. Illumination and detection axes 22 and 24 are shown in FIGS. 10-13, and it will be understood that other elements of the applanation detection system described in connection with FIGS. 3 and 6 are used in subsystems 50 and 70 even though such elements are not shown FIGS. 10-13.

In the embodiment depicted in FIGS. 10-11, subsystem 50 is configured the same as subsystem 10 except that a different nosepiece 52 is provided in place of nosepiece 12. Nosepiece 52 includes a nosepiece body 53 having an entrance end 56, and exit end 57, and a radially stepped guide passage 60 extending through nosepiece body 53 from entrance end 56 through exit end 57. Nosepiece 52 further includes a fluid discharge tube 54 received by guide passage 60 and arranged coaxially with the guide passage. Fluid discharge tube 54 defines a fluid discharge passage 55 configured to discharge a fluid pulse along fluid pulse axis 20. In accordance with the present embodiment, fluid discharge tube 54 is movable along fluid pulse axis 20 relative to nosepiece body 53. Illumination axis 22 and detection axis 24 converge with fluid pulse axis 20 at target point P located not less than 11 mm beyond the exit end 57 of nosepiece body 53 as measured along the fluid pulse axis. As may be understood with reference to FIG. 11, fluid discharge tube 54 is axially displaced to temporarily extend beyond the exit end 57 of nosepiece body 53 toward target point P to discharge a fluid pulse at a working distance of less than 11 mm. For example, discharge tube 54 may extend approximately 3 mm beyond exit end 57 when discharging a fluid pulse.

In the embodiment of FIGS. 10-11, fluid discharge tube 54 is displaced by force from fluid (e.g. air) pumped into an entrance end of tube 54 by a communicating pump mechanism (not shown) to generate a fluid pulse. Fluid discharge tube 54 may include a flange 66 near its entrance end for providing increased surface area to force the tube forward under fluid pressure. Flange 66 may engage a limit wall 62 of guide passage 60 to limit forward travel of the discharge tube. Discharge tube 54 may be returned to its original retracted position of FIG. 10 by suction created by return of the pump mechanism after the fluid pulse is generated. Alternatively, an active pneumatic return may be implemented by pumping air into the volume between flange 66 and limit wall 62. A fluid exit end of discharge tube 54 may be provided with a tapered lip 69 defining an abutment rim 68 for abutment with a radial seat 64 formed in passage 60 adjacent exit end 57 of nosepiece body 53, thereby limiting return travel of discharge tube 54. As seen in FIG. 10, the fluid exit end of tube 54 may be arranged flush with exit end 57 of nosepiece body 53 in the retracted position.

In the embodiment depicted in FIGS. 12-13, subsystem 70 is configured the same as subsystem 10 except that a different nosepiece 72 is provided in place of nosepiece 12, and the subsystem further comprises a drive motor as described below for moving a discharge tube 74 of nosepiece 72. Nosepiece 72 includes a nosepiece body 73 having an entrance end 76, and exit end 77, and a radially stepped guide passage 80 extending through nosepiece body 73 from entrance end 76 through exit end 77. Nosepiece 72 further includes fluid discharge tube 74 received by guide passage 80 and arranged coaxially with the guide passage. Fluid discharge tube 74 defines a fluid discharge passage 75 configured to discharge a fluid pulse along fluid pulse axis 20. Fluid discharge tube 74 is movable along fluid pulse axis 20 relative to nosepiece body 73 from a retracted position shown in FIG. 12 to an extended discharge position shown in FIG. 13. Illumination axis 22 and detection axis 24 converge with fluid pulse axis 20 at target point P located not less than 11 mm beyond the exit end 77 of nosepiece body 73 as measured along the fluid pulse axis. Fluid discharge tube 54 is axially displaced as depicted in FIG. 13 to temporarily extend beyond the exit end 57 of nosepiece body 53 toward target point P to discharge a fluid pulse at a working distance of less than 11 mm. For example, discharge tube 74 may extend approximately 3 mm beyond exit end 77 when discharging a fluid pulse.

In the embodiment of FIGS. 12-13, fluid discharge tube 74 is displaced by force from a drive motor. In the example shown, discharge tube 74 is incorporated into an armature of a solenoid drive mechanism in the manner of a solenoid plunger. More particularly, an armature 90 is provided about discharge tube 74, and a solenoid coil winding 92 is provided within nosepiece body 73. Coil 92 is connected by leads 94 to a solenoid drive 96. Consequently, coil 92 may be selectively energized to drive armature 90 and tube 74 forward as shown in FIG. 13. Solenoid drive 96 may be commanded to energize coil 92 during a 10-15 msec "dead time" known to occur while a coil of the heavier pump mechanism is energized upon achievement of alignment with the cornea. A forward end of armature 90 may engage a limit wall 82 of guide passage 80 to limit forward travel of the discharge tube. The solenoid may be driven to return discharge tube 74 to its original retracted position shown in FIG. 12 by reversing the drive current and by making armature 90 a magnet.

The embodiments of FIGS. 10-13 are advantageous from the standpoint that interference from long eyelashes may be avoided because the discharge tube 54 or 74 extends instantaneously and the fluid pulse is discharged before a blink reflex occurs.

While the invention has been described in connection with exemplary embodiments, the detailed description is not intended to limit the scope of the invention to the particular forms set forth. The invention is intended to cover such alternatives, modifications and equivalents of the described embodiment as may be included within the spirit and scope of the invention.

LIST OF REFERENCE NUMERALS

1 Subsystem (prior art)
2 Nosepiece (prior art)
3 Nosepiece body (prior art)
4 Fluid discharge tube (prior art)
5 Fluid discharge passage (prior art)
6 Entry end of nosepiece (prior art)
7 Exit end of nosepiece (prior art)
8 Nosepiece flange (prior art)
10, 50, 70 Subsystem
12, 52, 72 Nosepiece
13, 53, 73 Nosepiece body
14, 54, 74 Fluid discharge tube
15, 55, 75 Fluid discharge passage
16, 56, 76 Entry end of nosepiece
17, 57, 77 Exit end of nosepiece 18, 58, 78 Nosepiece flange
19 Tapered region of nosepiece
20 Fluid pulse axis
22 Illumination axis
24 Detection axis
26 Emitter
28 Sleeve
30 Aperture stop tube
32 Window
34 Window
36 Aperture stop tube
38 Focusing lens
40 Aperture tube
42 Detector
60, 80 Guide passage
62, 82 Limit wall in guide passage
64 Radial seat in guide passage
66 Flange on fluid discharge tube
68 Abutment rim on fluid discharge tube
69 Tapered lip on fluid discharge tube
90 Armature
92 Coil
94 Leads
96 Solenoid drive
A1 Angle between illumination axis and fluid pulse axis
A2 Angle between detection axis and fluid pulse axis
D Working distance
P Target point
R Reference point

What is claimed is:

1. A subsystem for use in an ophthalmic instrument, the subsystem comprising:

a nosepiece including an exit end and a fluid discharge passage configured to discharge a fluid pulse from the exit end of the nosepiece along a fluid pulse axis;

an emitter arranged and configured to provide a collimated beam along an illumination axis converging with the fluid pulse axis at a target point located a predetermined distance beyond the exit end of the nosepiece along the fluid pulse axis; and a detector arranged on a detection axis, the detection axis converging with the illumination axis and the fluid pulse axis at the target point;

wherein the predetermined distance is in a range from 8 mm through 9 mm.

2. The subsystem according to claim 1, wherein the nosepiece is tapered adjacent the exit end.

3. A method of causing applanation of a cornea, the method comprising the steps of:

providing a nosepiece including an exit end and a fluid discharge passage configured to discharge a fluid pulse from the exit end of the nosepiece along a fluid pulse axis;

aligning the nosepiece relative to the cornea such that the fluid pulse axis is normal to an apex of the cornea and the exit end of the nosepiece is aligned such that the exit end of the nosepiece is less than 9 mm from the apex of the cornea as measured along the fluid pulse axis;

discharging a fluid pulse from the exit end of the nosepiece along the fluid pulse axis, wherein the fluid pulse causes applanation of the cornea.

* * * * *